(12) United States Patent
Zhang et al.

(10) Patent No.: US 7,605,916 B2
(45) Date of Patent: Oct. 20, 2009

(54) ONLINE ANALYTE DETECTION BY SURFACE ENHANCED RAMAN SCATTERING (SERS)

(75) Inventors: Jingwu Zhang, San Jose, CA (US); Sarah M. Ngola, Sunnyvale, CA (US); Xing Su, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 413 days.

(21) Appl. No.: 11/524,489

(22) Filed: Sep. 21, 2006

(65) Prior Publication Data

US 2008/0074661 A1 Mar. 27, 2008

(51) Int. Cl.
*G01J 3/44* (2006.01)
(52) U.S. Cl. ..................................... 356/301
(58) Field of Classification Search .............. 356/301; 435/6, 7.1
See application file for complete search history.

(56) References Cited

U.S. PATENT DOCUMENTS

| | | | |
|---|---|---|---|
| 5,184,192 A * | 2/1993 | Gilby et al. ................ 356/246 |
| 6,258,264 B1 * | 7/2001 | Gjerde et al. ............ 210/198.2 |
| 6,357,484 B1 * | 3/2002 | Semerdjian ................ 138/44 |
| 7,267,948 B2 * | 9/2007 | Vo-Dinh ....................... 435/6 |
| 2005/0074779 A1 * | 4/2005 | Vo-Dinh ....................... 435/6 |
| 2005/0250159 A1 * | 11/2005 | Su et al. ..................... 435/7.1 |

FOREIGN PATENT DOCUMENTS

| | | |
|---|---|---|
| WO | 97/27327 | 7/1997 |
| WO | 2005/030997 | 4/2005 |
| WO | 2005/065541 | 7/2005 |
| WO | 2005/114298 | 12/2005 |

OTHER PUBLICATIONS

DeVault et al, "Spatially focused deposition of capillary electrophoresis . . . ", Electrophoresis 2001, 22, pp. 2303-2311.*

* cited by examiner

*Primary Examiner*—L. G Lauchman
(74) *Attorney, Agent, or Firm*—Pillsbury Winthrop Shaw Pittman LLP

(57) ABSTRACT

Devices and methods for separating and detecting analytes in a sample. The separation can be accomplished utilizing capillary electrophoresis (CE) or high-performance liquid chromatography (HPLC). The detection can be accomplished by surface enhanced Raman scattering.

40 Claims, 9 Drawing Sheets

Capillary

SERS-active packing material

Frits (a)   (b)   (c)   (d)

(a) SERS-active metal particles
(b) SERS-active metal particles with a thin layer of silica or other non-conducting materials
(c) Support particles (e.g. silica or latex beads) surrounded by SERS-active metal particles
(d) Support particles surrounded by SERS-active metal particles with an insulating layer

ONLINE ANALYTE DETECTION BY SURFACE ENHANCED RAMAN SCATTERING (SERS)

FIELD OF INVENTION

The embodiments of the invention relate to the separation and detection of analytes by surface enhanced Raman scattering (SERS). The online detection of an analyze includes separating a sample including analytes prior to detection. The separation can be accomplished utilizing capillary electrophoresis (CE) or high-performance liquid chromatography (HPLC). The invention transcends several scientific disciplines such as polymer chemistry, biochemistry, molecular biology, medicine and medical diagnostics.

BACKGROUND

The ability to detect and identify trace quantities of analytes has become increasingly important in virtually every scientific discipline, ranging from part per billion analyses of pollutants in sub-surface water to analysis of cancer treatment drugs in blood serum. Raman spectroscopy is one analytical technique that provides rich optical-spectral information, and surface-enhanced Raman spectroscopy (SERS) has proven to be one of the most sensitive methods for performing quantitative and qualitative analyses. A Raman spectrum, similar to an infrared spectrum, consists of a wavelength distribution of bands corresponding to molecular vibrations specific to the sample being analyzed (the analyte). In the practice of Raman spectroscopy, the beam from a light source, generally a laser, is focused upon the sample to thereby generate inelastically scattered radiation, which is optically collected and directed into a wavelength-dispersive spectrometer in which a detector converts the energy of impinging photons to electrical signal intensity.

Among many analytical techniques that can be used for chemical structure analysis, Raman spectroscopy is attractive for its capability to provide rich structure information from a small optically-focused area or detection cavity. Compared to a fluorescent spectrum that normally has a single peak with half peak width of tens of nanometers to hundreds of nanometers, a Raman spectrum has multiple bonding-structure-related peaks with half peak width of as small as a few nanometers.

Although Raman spectroscopy has proven effective for identifying certain Raman active compounds, up till now, analyzing a sample or samples containing multiple Raman active compounds has been a time consuming and labor intensive task.

DETAILED DESCRIPTION

Figure 1:
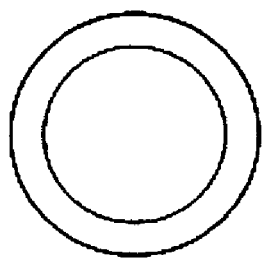
FIG. 1 shows one embodiment of a flow-through SERS cell for separating a sample and for SERS measurement.
Figure 1:
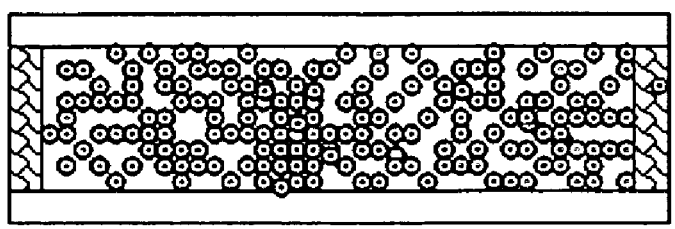
Figure 1:
Figure 1:

As used in the specification and claims, the singular forms "a", "an" and "the" include plural references unless the context clearly dictates otherwise. For example, the term "a nanoparticle" may include a plurality of nanoparticles unless the context clearly dictates otherwise.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "analyte", "target" or "target molecule" refers to a molecule of interest that is to be analyzed. The analyte may be a Raman active compound or a Raman inactive compound. Further, the analyte could be an organic or inorganic molecule. Some examples of analytes may include a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The analyte molecule may be fluorescently labeled DNA or RNA.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the substrate of the array. The probe or probe molecule is typically a nucleotide, an oligonucleotide, or a protein, including, for example, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

The phrase "SERS active material," "SERS active particle," or "SERS active cluster" refers to a material, a particle or a cluster of particles that produces a surface-enhanced Raman scattering effect. The SERS active material or particle generates surface enhanced Raman signal specific to the analyte molecules when the analyte-particle complexes are excited with a light source as compared to the Raman signal from the analyte alone in the absence of the SERS active material or SERS active particle. The enhanced Raman scattering effect provides a greatly enhanced Raman signal from Raman-active analyte molecules that have been adsorbed onto certain specially-prepared SERS active surfaces. The SERS active surface could be planar or curved. Typically, the SERS active surfaces are metal surfaces. Increases in the intensity of Raman signal could be in the order of $10^4$-$10^{14}$ for some systems. SERS active material or particle includes a variety of metals including coinage (Au, Ag, Cu), alkalis (Li, Na, K), Al, Pd and Pt. In the case of SERS active particle, the particle size of SERS active particles could range from 1 to 5000 nanometers, preferably in the range of 5 to 250 nanometers, more preferably in the range of 10 to 150 nanometers, and most preferably 40 to 80 nanometers.

The term "capture particle" refers to a particle that can capture an analyte. The capture particle could be a coinage metal nanoparticle with surface modification to allow strong physical and/or chemical adsorption of analyte molecules and to allow adhesion of "enhancer particles" by electrostatic attraction, through specific interaction using a linker such as antibody-antigen, DNA hybridization, etc. or through the analyte molecule.

The term "enhancer particle" refers to a SERS active particle with suitable surface modification, a linker or an analyte which combines with a capture particle to form an aggregate. In case the capture particle is positively charged, then a negatively charged SERS active particle can be used as an enhancer particle without a linker, and vise versa. In case the capture particle has an antigen or an antibody, then a SERS active particle having a complimentary linker, namely, an antibody or an antigen, could be used as an enhancer particle.

As used herein, the term "colloid" refers to nanometer size metal particles suspending in a liquid, usually an aqueous solution. In the methods of the invention, the colloidal particles are prepared by mixing metal cations and reducing agent in aqueous solution prior to heating. Typical metals contemplated for use in the practice of the invention include, for example, silver, gold, platinum, copper, and the like. A variety of reducing agents are contemplated for use in the practice of the invention, such as, for example, citrate, borohydride, ascorbic acid and the like. Sodium citrate is used in certain embodiments of the invention. Typically, the metal cations and reducing agent are each present in aqueous solution at a concentration of at least about 0.5 mM. After mixing the metal cations and reducing agent, the solution is heated for about 30 minutes. In some embodiments, the solution is heated for about 60 minutes. Typically, the solution is heated to about 95° C. In other embodiments, the solution is heated to about 100° C. Heating of the solution is accomplished in a variety of ways well known to those skilled in the art. In some embodiments, the heating is accomplished using a microwave oven, a convection oven, or a combination thereof. The methods for producing metallic colloids described herein are in contrast to prior methods wherein a boiling silver nitrate solution is titrated with a sodium citrate solution. This titration method can produce one batch of silver particles with adequate Raman enhancement to dAMP in about 10 attempts, and the other batches have low or no Raman activity at all. However, by employing the methods of the invention, an average SERS signal enhancement of 150% is observed relative to colloids prepared from the titration method.

Figure 2:
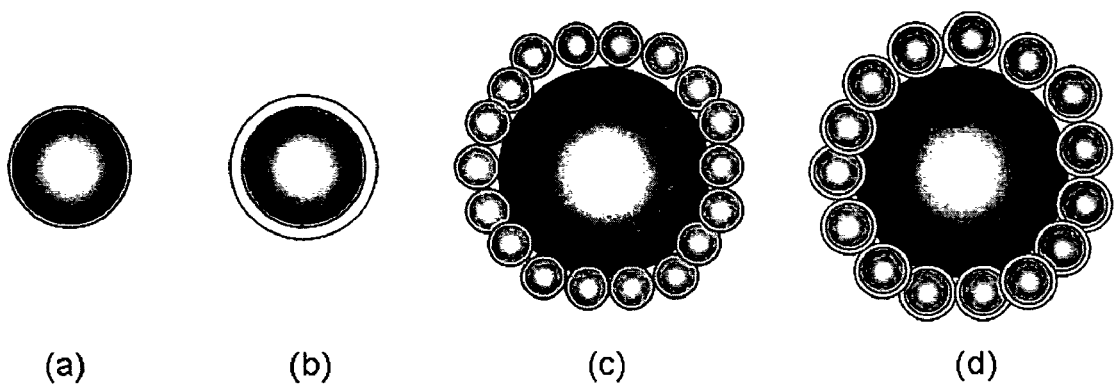
FIG. 2(a) shows an embodiment of a metal particle that can be used as a SERS active packing material.
FIG. 2(b) shows an embodiment of a metal particle insulated with a thin layer of silica or other non-conducting material that can be used as a SERS active packing material.
FIG. 2(c) shows an embodiment of a support bead made from an insulating material such as silica or latex surrounded by metal particles that can be used as a SERS active packing material.
FIG. 2(d) shows an embodiment of a support bead made from an insulating material such as silica or latex surrounded by metal particles that are insulated with a thin layer of silica or other non-conducting material that can be used as a SERS active packing material.

The metallic colloids could be modified by attaching an organic molecule to the surface of the colloids to provide desirable affinity for the analyte molecules for optimal separation and detection. Organic molecules contemplated would typically be less than about 500 Dalton in molecular weight, and are bifunctional organic molecules. As used herein, a "bifunctional organic molecule" means that the organic molecule has a moiety that has an affinity for the metallic surface, and a moiety that has an affinity for the analyte molecules. The colloids can be used either individually, or as aggregates as shown in FIG. 2.

Organic molecules contemplated for use include molecules having any moiety that exhibits an affinity for the metals contemplated for use in the methods of the invention (i.e., silver, gold, platinum, copper, aluminum, and the like), and any moiety that exhibit affinities for biomolecules. For example, with regard to silver or gold affinity, in some embodiments, the organic molecule has a sulfur containing moiety, such as for example, thiol, disulfide, and the like. With regard to affinity for an analyte molecule such as a polynucleotide, for example, the organic molecule has a carboxylic acid moiety. In certain embodiments, the organic molecule is thiomalic acid, L-cysteine diethyl ester, S-carboxymethyl-L-cysteine, cystamine, meso-2,3-dimercaptosuccinic acid, and the like. It is understood, however, that any organic molecule that meets the definition of a "bifunctional organic molecule", as described herein, is contemplated for use in the practice of the invention. It is also understood that the organic molecule may be attached to the metallic surface and the biomolecule either covalently, or non-covalently. Indeed, the term "affinity" is intended to encompass the entire spectrum of chemical bonding interactions.

This surface modification of metallic colloids provides certain advantages in SERS detection analyses. For example, the surfaces of the metallic colloids could be tailored to bind to a specific biomolecule or the surfaces can be tailored to differentiate among groups of proteins based on the side chains of the individual amino acid residues found in the protein.

SERS may be used to detect the presence of a particular target analyte, for example, glucose, a nucleic acid, oligonucleotide, protein, enzyme, antibody or antigen. SERS may also be used to screen bioactive agents, i.e. drug candidates, or to detect agents like pollutants in food and water (including water samples from rivers, lakes, ocean, aquifers, etc). SERS can also be potentially useful in monitoring chemical reactions and identifying the products of the reaction.

The terms "spectrum" or "spectra" refer to the intensities of electromagnetic radiation as a function of wavelength or other equivalent units, such as wavenumber, frequency, and energy level.

The term "separation cell" refers to a cell configured to hold a sample while a sample is separated within the cell. The cell may be part or all of another cell, for example a SERS cell.

Described are devices and methods for separating and detecting analytes in a sample. The separation can be accomplished utilizing capillary electrophoresis (CE) or high-performance liquid chromatography (HPLC). The detection can be accomplished by surface enhanced Raman scattering.

One embodiment is a device that includes a separation cell configured to separate analytes in a sample, and a surface enhanced Raman scattering (SERS) cell. The SERS cell includes SERS active particles, wherein the separation cell and the SERS cell are configured to permit analytes in the sample to flow through the separation cell into the SERS cell.

Preferably, the separation cell includes capillary electrophoresis (CE). Preferably, the separation cell includes capillary or nanobore high-performance liquid chromatography (HPLC). Preferably, the device also includes a SERS detector. Preferably, the separation cell includes SERS active particles.

Preferably, the SERS active particles include metal particles insulated with a non-conducting material. Alternatively, preferably the SERS active particles include an insulating support particle surrounded by metal particles. Preferably, the support particle is made from or includes an insulating material. The metal particle surrounding the support particle may be surrounded by an insulating non-conducting material. Preferably, the SERS active particles include gold, silver, copper, lithium, sodium, potassium, palladium, platinum, or aluminum.

Another embodiment is a device that includes a separation cell including surface enhanced Raman scattering (SERS) active particles, wherein the cell is configured to separate analytes in a sample flowing through the separation cell; and a SERS detector configured to collect the Raman spectra of analytes within the separation cell.

Preferably, the separation cell includes capillary electrophoresis (CE). Preferably, the separation cell includes capillary or nanobore high-performance liquid chromatography (HPLC).

Yet another embodiment is a device that includes a separation cell configured for capillary electrophoresis (CE); and a Raman detector configured to collect the Raman spectra of analytes flowing through the separation cell.

Preferably, the separation cell includes SERS active particles. Preferably, the SERS active particles include metal particles insulated with a non-conducting material.

Alternatively, preferably, the SERS active particles including an insulating support particle surrounded by metal particles. The metal particles may include gold, silver, copper, lithium, sodium, potassium, palladium, platinum, or aluminum. The insulating support particle preferably includes silica or latex. The metal particles surrounding the insulating support particle may be surrounded by insulated non-conducting material.

Another embodiment is a device that includes a separation cell configured to perform capillary or nanobore high-performance chromatography (HPLC); and a Raman detector configured to collect the Raman spectra of analytes flowing through the separation cell.

Preferably, the separation cell includes SERS active particles. Preferably, the SERS active particles have been modified to provide affinity for various analytes.

An embodiment of a method of collecting the Raman spectra of analytes in a sample includes introducing a sample into a cell configured to perform capillary electrophoresis (CE); separating a sample including analytes by CE; and collecting the Raman spectra of analytes in a sample using a Raman detector, wherein the Raman detector is located in-line with the cell configured to perform CE.

Another embodiment is a method of collecting the Raman spectra of analytes in a sample. The method includes introducing a sample into a cell configured to perform high-performance chromatography (HPLC); separating a sample including analytes by HPLC; and collecting the Raman spectra of analytes in a sample using a Raman detector.

SERS measurements typically involve manually mixing silver or gold colloids with an analyte solution and in most cases introducing an electrolyte solution (e.g. NaCl) to cause the metal particles to aggregate into clusters with a random structure. The aggregation continues during the measurement, which can result in SERS signal decay. Accordingly, to make the measurements more reproducible, the reading is preferably taken at a fixed time after reagent mixing. Further, for analyte samples containing multiple components, separation is preferably performed before each fraction is analyzed by manual SERS measurement.

The described methods and systems allow for the automation of both the separation of a sample including multiple components and the SERS measurements of the separated sample. The automation of these procedures as disclosed can allow for: 1) high analyte throughput thanks to automation; 2) more reproducible results due to fixed particle arrangement in the detector; 3) seamless interface with separation methods such as CE and Capillary and Nanobore HPLC.

Prior to detecting the analyte(s) by SERS, preferably a sample containing the analyte(s) is separated in an inline manner. Preferred inline separation methods include CE and Capillary HPLC for which a large selection of commercial instruments is available and numerous methods have been developed for various samples.

CE typically involves the injection of a sample that contains one or more analytes, into a thin capillary. A potential is then applied along the length of the capillary to electrophoretically draw the materials contained within the sample through the capillary. The analytes present in the sample then separate from each other based upon differences in their electrophoretic mobility within the capillary. Such differences in electrophoretic mobility typically result from differences in the charge and/or size of a compound. Other factors can also affect the electrophoretic mobility of a given analyte, such as interactions between the analyte and the capillary walls, interactions with other analytes, conformation of the analytes, and the like. CE methods have traditionally employed fused silica capillaries for the performance of these electrophoretic separations. Alternatively, the fused silica capillary can be replaced by an etched channel in a solid planer substrate, e.g., a glass or silica slide or substrate. A covering layer or substrate can provide the last wall of the capillary. CE can be applied to a variety of separation problems including inorganic ions, amino acids, drugs, vitamins, carbohydrates, peptides, proteins, nucleic acids, nucleic acids, polynucleotides, etc.

High-performance liquid chromatography (HPLC) is a form of liquid chromatography used to separate compounds in solution. HPLC instruments include a separation cell (column) that contains a stationary phase, and a pump for moving a sample through the cell. The sample is a mobile phase. Compounds are separated by injecting a plug of the sample mixture into the column. The different components in the mixture pass through the column at different rates due to differences in their partitioning behavior between the mobile liquid phase and the stationary phase. In capillary HPLC, a capillary is used for the separation cell. Unlike CE, which uses a potential to electrophoretically draw the sample through the capillary, capillary HPLC uses one or more pumps to drive the mobile phase which carries the sample through the capillary.

HPLC cells or columns are typical cylindrical in shape. Cylindrical columns from different materials and with a range of internal diameters are readily available commercially. The inner diameter (i.d.) of HPLC columns preferably range from <25 µm for open tubular liquid chromatography to over 10 mm for preparative HPLC. For integration with SERS detection, nanobore columns (25 µm<i.d.<100 µm) and capillary columns (100 µm<i.d.<1 mm) are preferable.

Once the sample containing the analyte(s) is separated, a SERS detector can be utilized to obtain the Raman spectra of the analyte(s). A SERS cell is a cell configured to hold a sample while a SERS detector obtains the Raman spectra of the sample within the cell. Preferably, the SERS cell is in line with the cell or cells utilized for the separation. In-line means that the sample can flow from the separation portion of the apparatus into the SERS cell. The SERS cell may be the same cell used for separating the sample. For example, the inline SERS cell may be a section of the capillary used for CE or capillary HPLC. In other words, the capillary utilized for the separation may flow the sample directly into a separate section of the capillary or any other SERS suitable cell. Preferably, the SERS cell is the same cell used for separating the sample and SERS active particles are utilized as the stationary phase for sample separation.

Preferably, the SERS cell is configured to allow the sample to flow out of the SERS cell once the SERS spectra has been obtained to allow for the next sample to flow into the cell. For example, a capillary SERS cell would allow the sample to continue down the capillary and into a collection cell where the sample can be disposed of or held onto for further analysis.

Alternatively, the sample may be allowed to continue into other detector cells placed in-line with the SERS cell for analyzing the sample or the SERS cell may include these other detectors. Preferred detectors include mass spectrometers (MS) and a UV-Vis detector. The UV-vis detector can also be placed before the SERS cell.

FIG. 1 shows one embodiment of a flow-through SERS cell for separating a sample and for SERS measurement. The cell includes a capillary packed with SERS active particles that are also used as stationary phase for separating a sample. Preferably the SERS active particles are metal particles as shown in FIG. 2(a), insulated SERS active metal particles as shown in FIG. 2(b), support particles surrounded by SERS active metal particles as shown in FIG. 2c, or support particles surrounded by insulated SERS active metal particles as shown in FIG. 2(d). Frits are used at both ends of capillary to prevent movement of the packed nanoparticles. For SERS cells to be connected or part of capillary electrophoresis separation, the capillary diameter is preferably 5 μm to 250 μm in diameter. More preferably, the capillary diameter is 100 μm to 150 μm in diameter. Most preferably the capillary diameter is 20 μm to 100 μm in diameter.

For SERS cells in connection with or part of capillary HPLC, the column inner diameter is preferably 100 μm to 1000 μm. More preferably, the capillary diameter is 200 μm to 750 um. Most preferably the capillary diameter is 250 μm to 500 um. Moreover, nanobore column HPLC, with a column inner diameter typically ranging from 25 μm to 100 μm can be used in series with or as part of SERS cell of the same inner diameter.

FIG. 2(a)-FIG. 2(d) show four embodiments of a SERS active packing material that can be used for CE and HPLC. FIG. 2(a) shows a SERS active metal particle. FIG. 2(b) shows a SERS active metal particle insulated with a thin layer of silica or other non-conducting material. Insulated packing materials are preferably used in CE to avoid electric conduction along the stationary phase. When silica is used as the insulating coating, further modification of the surface can be easily accomplished with well-known silica chemistry. However, it is preferable to keep the insulating layer and the addition modification layer sufficiently thin (less than about 5 nm, preferably less than 3 nm) to maintain a strong SERS effect on the analytes adsorbed on the packing materials. If capillary or nanobore HPLC is used in connection with the SERS cell, SERS nanoparticles without the insulating layer can be used. To avoid exceedingly high pressure in the capillary (especially in the case of HPLC), the metal particles with or without the insulating layer are preferably first adsorbed onto supporting particles as shown in FIG. 2(c) and FIG. 2(d).

FIG. 2(c) shows a SERS active bead in which a support bead made from an insulating material such as silica or latex is surrounded by metal particles. The metal particles may have a thin insulating layer such as silica with desired functional groups or length of alkyl chains attached as shown in FIG. 2(d). These SERS active beads can be used as a stationary phase for separation and/or for analyte Raman signal enhancement.

Preferred metals for the particles include coinage (Au, Ag, Cu), alkalis (Li, Na, K), Al, Pd and Pt. More preferred metals include silver and gold particles for their strong SERS effect and chemical stability. Because of their strong reactivity with water, the use of alkalis metals is preferably limited to certain organic mobile phases.

The diameters of the metal particles preferably range from 10 to 200 nm. More preferably, the diameters of the metal particles range from 20 nm to 150 nm. Most preferably, the diameters of the metal particles range from 40 nm to 80 nm.

Alternatively, preferably the diameters of the SERS active beads range from 1 to 12 μm. More preferably, the diameters of the SERS active beads range from 2 to 7 μm. Most preferably, the diameters of the SERS active beads range from 3 to 5 μm.

Figure 3:
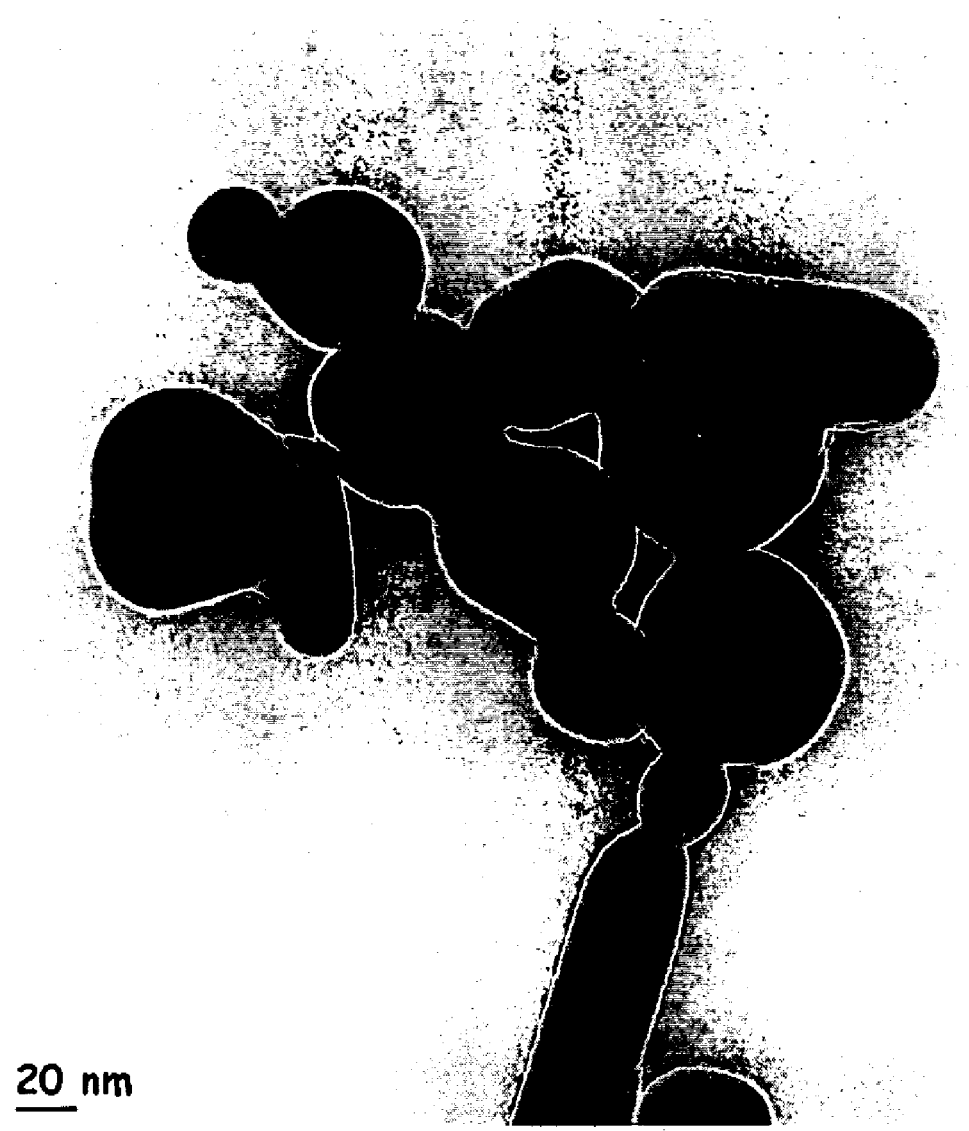
FIG. 3 shows a TEM image of silver particles nanoparticles optimized for SERS measurements with an average size of 50 nm.

FIG. 3 shows a TEM image of silver particles nanoparticles optimized for SERS measurements with an average size of 50 nm. These particles may be used to coat large silica or latex support beads to form SERS active beads.

Figure 4:
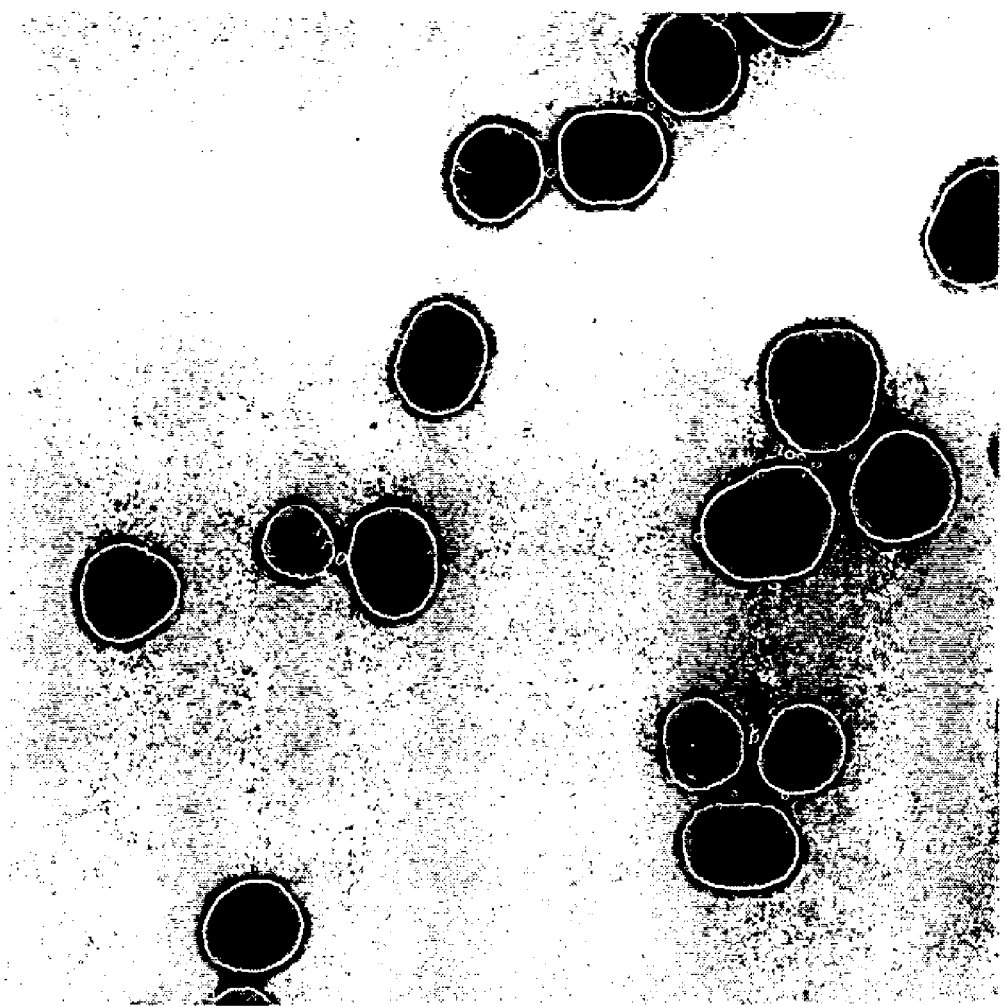
FIG. 4 shows a transmission electron microscope (TEM) image of silver nanoparticles coated with a layer of silica.

FIG. 4 shows a transmission electron microscope (TEM) image of silver nanoparticles coated with a layer of silica. As previously described, these particles can be used as a packing material when electrophoresis is used. The insulating layer can be made sufficiently thin so that the particles can still generate a strong SERS effect.

The silver nanoparticles can be prepared as follows: To a 250 mL round bottom flask equipped with a stirring bar, 100 mL de-ionized water and 0.200 mL of a 0.500 M silver nitrate solution is added. The flask is shaken to thoroughly mix the solution. 0.136 mL of a 0.500 M sodium citrate solution is then added to the flask using a 200 μl pipette. The flask is then placed in a heating mantle and the stirrer is set at medium speed. A water cooled condenser is attached to the flask and the heating commenced. The heating mantle is applied at maximum voltage, resulting in boiling of the solution between 7 and 10 minutes. Color changes occur within 120 seconds of boiling. The heating is stopped after 60 minutes, the solution is cooled to room temperature and the resulting colloidal suspension is transferred to a 100 mL glass bottle for storage.

The silver particles can be further coated with a layer of silica by using a modified Stöber process. In a 50 mL plastic centrifuge tube, add 15 mL of ethanol, 80 μL of 10% tetraethylorthosilicate (TEOS) in ethanol and 4 mL of SERS silver particles at total silver concentration of 10 mM. The solution is mixed well before adding 0.5 mL 28% ammonium hydroxide to initiate the hydrolysis of TEOS. After 60 min, the suspension is divided into two 50 mL centrifuge tubes of equal volume (10 mL). 30 mL of 1 mM trisodium citrate is added to each tube. They are then centrifuged at 4500 g for 15 min with a swing-bucket rotor. The supernatant is then withdrawn and discarded. The silica coated silver particles are stored in ethanol or in an aqueous solution at a low ionic strength and pH<7.5 (such as 0.1×PBS buffer at pH=7.4).

Examination of the silver particles under TEM (shown as the black regions) showed that the particles are substantially coated with silica (shown as gray coating on the black regions) having a thickness of about 5 nm as shown in the TEM photograph in FIG. 3. The thickness of the silica coating can be controlled by varying the particle concentration or total surface area. Thinner silica coatings can be achieved by adding more silver particles. If the concentration of the original silver suspension is too low, centrifugation may be used to concentrate the particles before coating. A similar procedure can also be applied to coat gold particles.

Figure 5:
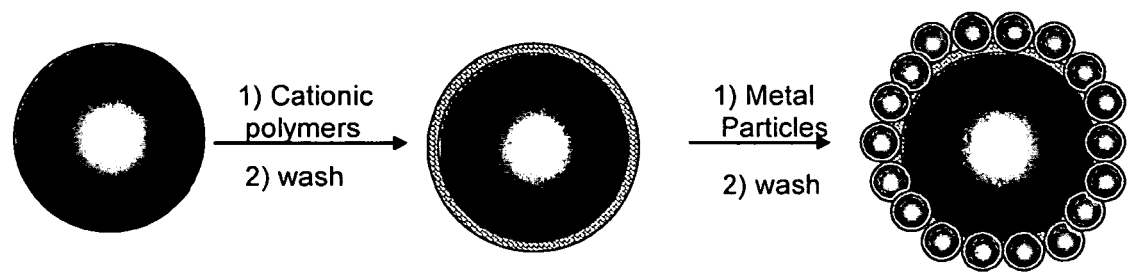
FIG. 5 illustrates how SERS active beads may be produced.

FIG. 5 shows the steps for making SERS active beads. SERS active beads can be prepared from positively charged latex support beads or negatively charged silica support beads. In the latter case, a cationic polymer will be first applied to make the beads positive.

For example, SERS active beads can be prepared from positively charged latex support beads by direct adsorption of negatively charged silver/gold particles or silica-coated metal particles as shown in FIG. 4. If silica beads are used as the support, a cationic polymer such as polyethyleimine and polyallyamine can be first applied to make the beads positive before negatively charged silver particles are added to form a complete coating. Alternatively, the silica beads may be derivitized with silane compounds with positively functional groups to reverse the charges on the silica surface. After coating with negatively charged silver nanoparticles, the free silver particles may be removed by centrifugation or filtration.

Figure 6:
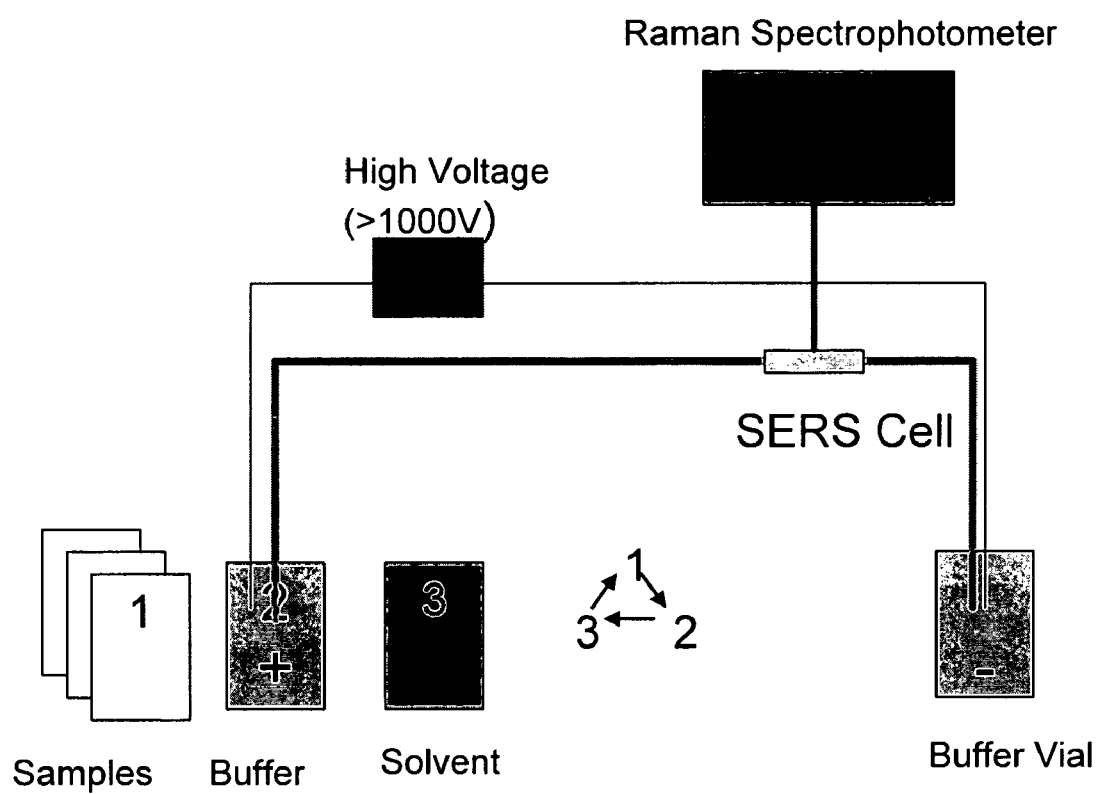
FIG. 6 is a schematic of an embodiment in which capillary electrophoresis is used to drive a sample solution through the SERS cell.

FIG. 6 is a schematic of an embodiment in which capillary electrophoresis is used to drive a sample solution through the SERS cell. The flow-through cell can be placed under the laser beam of a Raman spectrophotometer to collect the Surface Enhanced Raman Spectra of various Raman active compounds passing through the cell.

Samples can be injected sequentially using an automatic sampler. The autosamplers are commercially available from companies such as Agilent and Beckman Coulter. A typical autosampler for CE includes four trays; two sample trays and two buffer trays, each capable of holding 36, 48 or 96 well plates. The sample trays are primarily used for samples; the buffer trays hold the buffers and rinse solutions. The trays are usually arranged on two parallel tracks. Under normal operating conditions, the trays on the left are referred to as the inlet trays for the sample and buffer; the trays on the right are referred to as the outlet trays for sample and buffer. The positions of sample, buffer and rinsing solutions are controlled by a computer program. A rinsing solution is used to rinse the SERS cell to remove analyte molecules before the next injection. The composition of the rinsing solution depends on the nature of analytes and the surface properties of the packing materials in the SERS cell. For example, if the analytes are small molecules of relatively high hydrophobicity and the packing material is silica-coated silver particles derivitized with alkyl chain, a solution containing 90% ethanol or acetonitrile or isopropanol and 10% water can be used as the rinsing solution. If the analytes are charged molecules with relatively high solubility in water, the rinsing solution can be aqueous solution containing relatively high concentration of electrolytes such as NaCl, HCl or NaOH.

To prevent the contamination of the flow cell by hard-to-remove compounds in a sample, a pre-column packed with the same types of packing materials can be used.

A feature of this configuration is that a multi-component sample may be separated by capillary zone electrophoresis before reaching the SERS detector. A capillary of suitable length is installed before the SERS cell to separate the components according their electrophoretic mobility. The SERS cell is preferably relatively short (compared with the preceding separation capillary) so that a component can be washed out of the cell by the buffer solution before the arrival of the next component. The composition of the buffer solution is preferably optimized to provide adequate separation in the capillary column and sufficient Raman intensity in the detection cell.

Preferred buffer solutions may include one or more of the following: disodium phosphate/potassium dihydrogen phosphate, sodium borate, sodium citrate, sodium carbonate, Tris (hydroxymetryl)aminomthane (Tris), N'-2-Hydroxyethylpiperazine-N',2-ethanesulfonic acid (HEPES), Cacidylic acid, glycine, sodium hydroxide, hydrochloric acid, etc.

Figure 7:
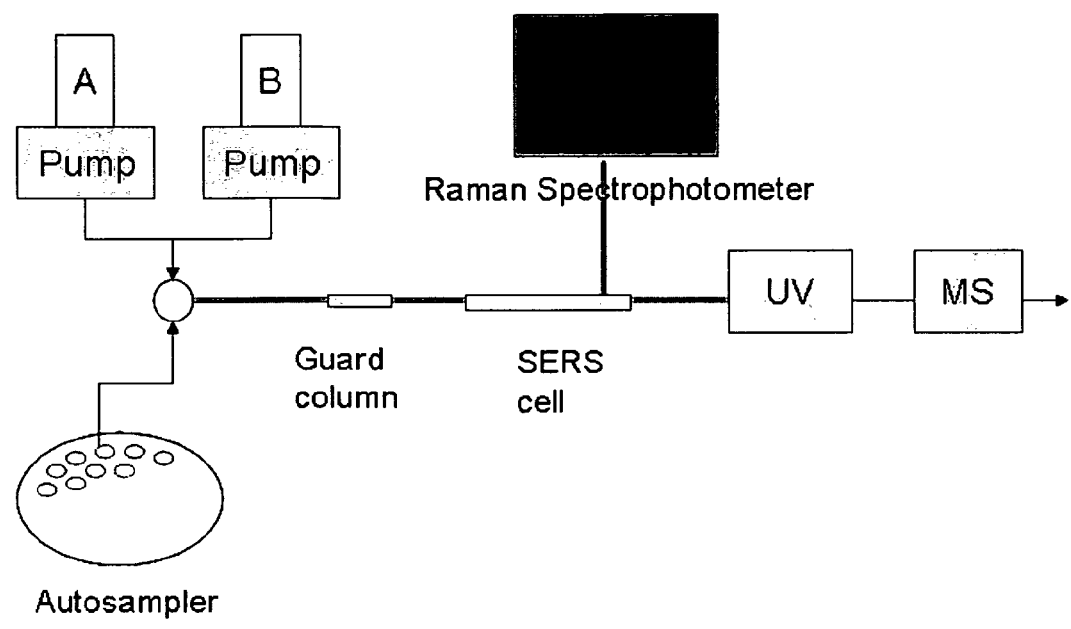
FIG. 7 is a schematic of an embodiment in which Capillary HPLC is used in combination with a SERS cell.

FIG. 7 is a schematic of an embodiment in which Capillary or Nanobore HPLC used in combination with a SERS cell. This embodiment may include a short capillary or nanobore column (as guard column) and a relatively long SERS cell. The SERS cell then functions as the separation column (as in chromatography) based on affinity of analytes to the metal particles. The surface of the metal particles can be modified to provide different degrees of affinity for various analytes. Syringe pumps or HPLC pumps with a flow splitter can be used to drive the liquid through the SERS cell. A Raman spectrometer can be used to collect the spectra of analytes near the end of the cell. Other detectors such as MS and UV-Vis detectors can also be used in sequence.

The surface of metal particles used as the packing material in the SERS cell can be modified in various ways to improve one or more types of interactions between the analyte molecules and the modified surface in order to achieve better separation and greater SERS signals. Three main types of interactions between the analytes and SERS substrate are utilized, as summarized below.

Electrostatic interaction: Silver and gold nanoparticles prepared by reduction of the metal ions with common reducing agents such as citrate and sodium borohydride have negative surface charges primarily due to the adsorption of major anions (citrate or $BH_4^-$) in solution. Those negatively charged nanoparticles can be used directly for analyzing most positively charged molecules as the strong electrostatic attraction brings the analyte molecules close to the particle surface. However, for analyzing negatively charged molecules, low SERS signal intensity is expected unless the electrostatic repulsion is overwhelmed by specific interactions between the molecules and the surface. To overcome this difficulty, the nanoparticles surface can be made to carry positive charges by adsorption of simple ions (e.g. protons and ferric ions), small molecules (e.g. thiol amine), polyelectrolytes (e.g. polyallylamine and polyethyleneimine) as well as very fine nanoparticles (e.g. hematite). Positively charged surface can also be generated by depositing a thin layer of inorganic phase such as hematite and titanium oxide which carry positive charges at neutral and low pH's.

Hydrophobic interaction: Most of large organic molecules of medical and environmental interest are generally at least partially hydrophobic. This is one of main reasons for the wide applicability of reverse phase HPLC as an analytical tool. An organic coating can be created on silver/gold particles to retain various analyte molecules as in the case of reverse phase chromatography. For example, alkyl chains of different lengths (from C4 to C18) can be grafted to gold particles or gold coated silver particles.

In other embodiments of the invention, other functional groups can also be introduced in the organic phase to include more specific interactions such as H-bonding and ion-pairing. The strong S—Au interaction can also be employed to introduce various functional groups into the hydrophobic layer around the particles. For example, bifunctional molecules of the type HS—R—X can be adsorbed on gold or gold coated silver surface, where X can be carboxyl, amine, hydroxyl, and so on, and R can be any type of hydrocarbon moiety with or without various functional groups to facilitate specific interactions with the analyte molecules. For example, the introduction of amine or positively charged ammonium groups will facilitate electrostatic interaction with negatively charged analyte molecules. Similarly, the presence of negatively charged functional groups such sulfate and phosphate can facilitate ion-pairing with positively charged analytes.

Alternatively in other embodiments of the invention, the metal nanoparticles can be coated with a thin layer of silica, as shown in FIG. 4, and then various organic molecules can be attached through the silanol. One facile approach is to use silane compounds of the type, X—R—Si(OCH$_3$)$_3$ or X—R—Si(OCH$_2$CH$_3$), where R can be alkyl or any hydrocarbon moiety with or without functional groups, X can be H or various functional groups such as —COOH, —NH$_2$, —N(CH$_3$)$_3^+$, etc. Organic solvent such as ethanol may used to dissolve the silane compounds before silica-coated silver or gold particles are added.

Specific interaction: Covalent bonding and other strong specific interactions such as hydrogen bonding between complimentary oligonucleic acid strands as well as antibody-antigen interaction can be used to bring the analyte molecules very close to the native or derivatized metal particle surface. For example, when analyzing thiol-containing compounds, gold nanoparticles or silver particles with a thin gold layer can be used as a SERS substrate to take the advantage of the strong S—Au interaction.

In other embodiments of the invention relating to analyzing proteins or peptides, the metal particles can be derivatized with ligands with strong affinity for the analytes as in the case of immobilized metal affinity chromatography (IMAC). Glutathione can be used for Glutathione-S-Transferase (GST)-proteins, and boronic acid or lectin for glycoproteins and polysaccharides as well as carbohydrates.

In the above cases, the Raman scattering from the affinity ligands should preferably be subtracted as follows. A background Raman spectrum of each modified particle in the absence of any analyte is recorded. Upon collection of a spectrum in the presence of analyte, the background spectrum is then subtracted out yielding peaks that can be attributed to the analyte in question. This can be done using a variety of commercially-available software. An examination of the change in background peaks can also provide information about the binding mode of the analyte. Changes in particular bands can be associated with functional groups in the background and indicate how the analyte is interacting with the nanoparticle. This is useful in fine-tuning the specificity of the nanoparticle for a particular analyte.

Figure 8:
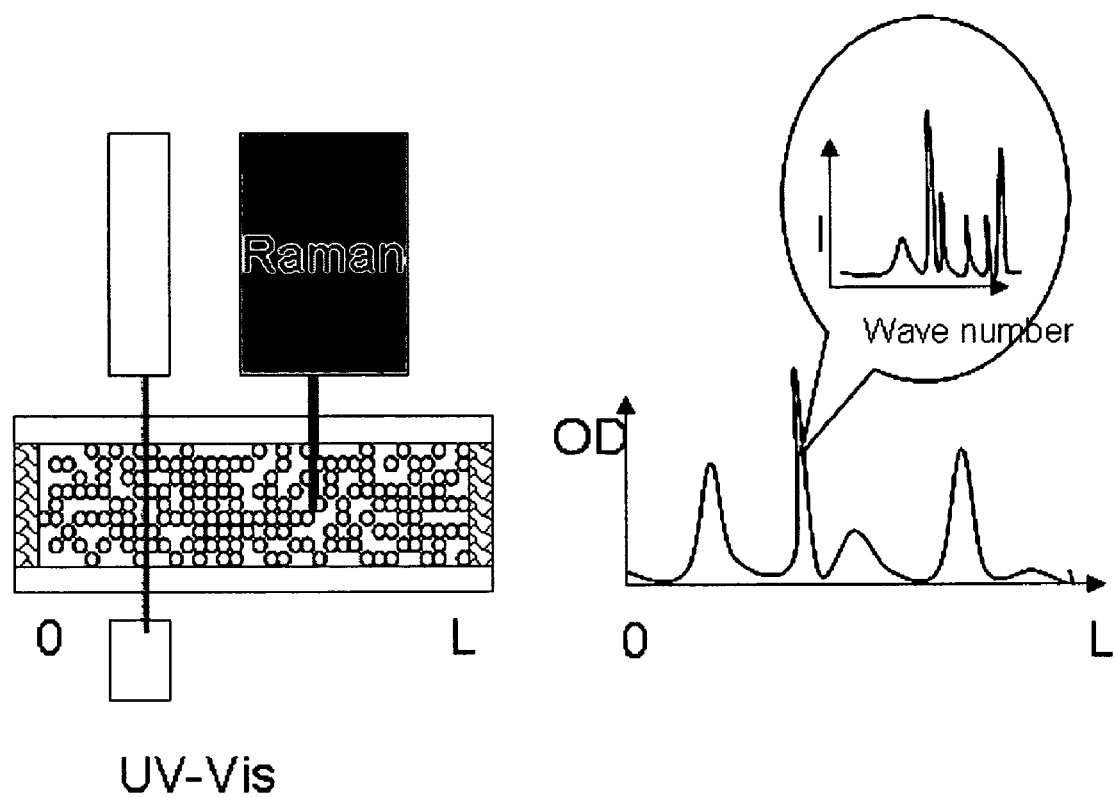
FIG. 8 is an embodiment in which separation and elution are controlled so that all the desired analytes are retained in the SERS cell but with good separation.

FIG. 8 is an embodiment in which separation and elution are controlled so that all the desired analytes are retained in the SERS cell but with good separation. The SERS cell can then be taken off line and scanned by a Raman spectrometer and other detection methods to determine the position (equivalent to elution time) and the Raman spectra of the analytes within the SERS cell.

Figure 9:
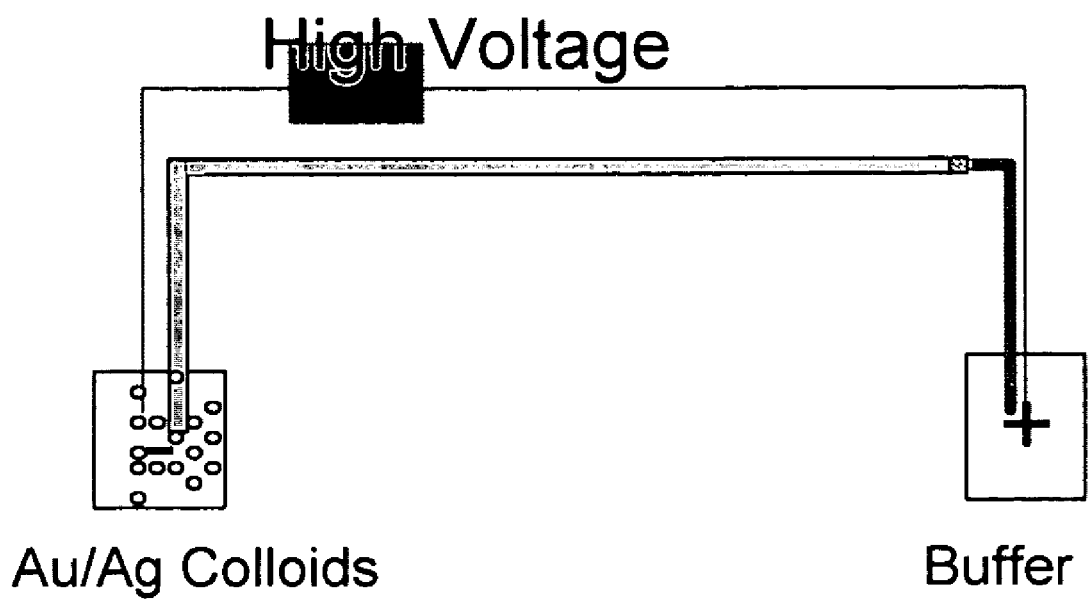
FIG. 9 illustrates one method for packing the metal particles into a capillary.

FIG. 9 illustrates one method for packing the metal particles and SERS-active beads into a capillary. In FIG. 9 one end of the capillary is blocked by a frit or porous membrane to retain the packing material and the other end is inserted into a suspension containing the metal colloids. A high voltage, preferably greater than 1000V, is applied to transport the colloidal particles into the capillary. After the desired packing density is achieved, the capillary is sectioned into suitable lengths and both ends are sealed with frits. Porous polymer monoliths are very convenient materials for this purpose. The porous polymers can be formed via UV-initiated free-radical polymerization. Both the position and the dimensions of the frit can be controlled using photo-masking to limit the polymerization to a particular area. Careful selection of the component monomers allows for the porosity of the polymers to be adjusted to the desired range.

The online detection system based on Surface Enhanced Raman Spectroscopy (SERS) as described in this invention can greatly increase the throughout of sample analysis. When the sample is a mixture, the combination of SERS detector with capillary electrophoresis and HPLC opens the possibility of sample separation and detection in sequence. Commercial applications of the invention include environmental toxicology and remediation, biomedicine, materials quality control, food and agricultural products monitoring, anesthetic detection, automobile oil or radiator fluid monitoring, hazardous spill identification, explosives detection, fugitive emission identification, medical diagnostics, detection and classification of bacteria and microorganisms both in vitro and in vivo for biomedical uses and medical diagnostic uses, monitoring heavy industrial manufacturing, ambient air monitoring, worker protection, emissions control, product quality testing, leak detection and identification, oil/gas petrochemical applications, combustible gas detection, H$_2$S monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia & sterilization gas detection, infectious disease detection and breath applications, body fluids analysis, pharmaceutical applications, drug discovery, telesurgery, and the like.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A device comprising:
 a separation cell configured to separate analytes in a sample; and
 a surface enhanced Raman scattering (SERS) cell comprising SERS active particles, wherein the separation cell and the SERS cell are connected by a fluid connection to permit analytes in the sample to flow through the separation cell into the SERS cell, wherein the SERS cell is a flow-through SERS cell and the device is an on-line detection device to detect the analytes in the sample as the analytes pass through the SERS cell.

2. The device of claim 1, wherein the separation cell comprises capillary electrophoresis (CE).

3. The device of claim 1, wherein the separation cell comprises capillary or nanobore high-performance liquid chromatography (HPLC).

4. The device of claim 1, further comprising a SERS detector.

5. The device of claim 1, wherein the separation cell comprises SERS active particles.

6. The device of claim 5, wherein the SERS active particles comprise metal particles insulated with a non-conducting material.

7. The device of claim 5, wherein the SERS active particles comprise a support particle surrounded by metal particles.

8. The device of claim 7, wherein the support particle comprises an insulating material.

9. The device of claim 7, wherein the metal particles are surrounded by insulating non-conducting material.

10. The device of claim 1, wherein the SERS active particles comprise gold, silver, copper, lithium, sodium, potassium, palladium, platinum, or aluminum.

11. A device comprising:
a separation cell comprising surface enhanced Raman scattering (SERS) active particles, wherein the cell is configured to separate analytes in a sample flowing through the separation cell; and
a SERS detector configured to collect the Raman spectra of analytes within the separation cell.

12. The device of claim 11, wherein the separation cell comprises capillary electrophoresis (CE).

13. The device of claim 11, wherein the separation cell comprises capillary or nanobore high-performance liquid chromatography (HPLC).

14. The device of claim 11, wherein the SERS active particles comprise metal particles insulated with a non-conducting material.

15. The device of claim 14, wherein the metal particles comprise gold, silver, copper, lithium, sodium, potassium, palladium, platinum, or aluminum.

16. The device of claim 14, wherein the non-conducting material comprises silica or latex.

17. The device of claim 11, wherein the SERS active particles comprise a support particle surrounded by metal particles.

18. The device of claim 17, wherein the metal particles comprise gold, silver, copper, lithium, sodium, potassium, palladium, platinum, or aluminum.

19. The device of claim 17, wherein the support particle comprises an insulating material.

20. The device of claim 17, wherein the metal particles are surrounded by insulating non-conducting material.

21. A device comprising:
a separation cell configured for capillary electrophoresis (CE); and
a Raman detector configured to collect the Raman spectra of analytes flowing through the separation cell, wherein the separation cell comprises SERS active particles.

22. The device of claim 21, wherein the SERS active particles comprise metal particles insulated with a non-conducting material.

23. The device of claim 22, wherein the metal particles comprise gold, silver, copper, lithium, sodium, potassium, palladium, platinum, or aluminum.

24. The device of claim 22, wherein the non-conducting material comprises silica or latex.

25. The device of claim 21, wherein the SERS active particles comprise a support particle surrounded by metal particles.

26. The device of claim 25, wherein the metal particles comprise gold, silver, copper, lithium, sodium, potassium, palladium, platinum, or aluminum.

27. The device of claim 25, wherein the support particle comprises an insulating material.

28. The device of claim 25, wherein the metal particles are surrounded by insulating non-conducting material.

29. A device comprising:
a separation cell configured to perform capillary or nanobore high-performance chromatography (HPLC); and
a Raman detector configured to collect the Raman spectra of analytes flowing through the separation cell, wherein the separation cell comprises SERS active particles.

30. The device of claim 29, wherein the SERS active particles have been modified to provide affinity for various analytes.

31. A method of collecting the Raman spectra of analytes in a sample comprising:
introducing a sample into a cell configured to perform capillary electrophoresis (CE);
separating a sample comprising analytes by CE; and
collecting the Raman spectra of analytes in a sample using a Raman detector, wherein the Raman detector is located in-line with the cell configured to perform CE, wherein the cell comprises SERS active particles.

32. The method of claim 31, wherein the SERS active particles comprise metal particles insulated with a non-conducting material.

33. The method of claim 32, wherein the metal particles comprise gold, silver, copper, lithium, sodium, potassium, palladium, platinum, or aluminum.

34. The method of claim 32, wherein the non-conducting material comprises silica or latex.

35. The method of claim 31, wherein the SERS active particles comprise a support particle surrounded by metal particles.

36. The method of claim 35, wherein the metal particles comprise gold, silver, copper, lithium, sodium, potassium, palladium, platinum, or aluminum.

37. The method of claim 35, wherein the support particle comprises an insulating material.

38. The method of claim 35, wherein the metal particles are surrounded by insulating non-conducting material.

39. A method of collecting the Raman spectra of analytes in a sample comprising:
introducing a sample into a cell configured to perform high-performance chromatography (HPLC);
separating a sample comprising analytes by HPLC; and
collecting the Raman spectra of analytes in a sample using a Raman detector, wherein the cell comprises SERS active particles.

40. The method of claim 39, wherein the SERS active particles have been modified to provide affinity for various analytes.

* * * * *

UNITED STATES PATENT AND TRADEMARK OFFICE
CERTIFICATE OF CORRECTION

PATENT NO. : 7,605,916 B2 Page 1 of 1
APPLICATION NO. : 11/524489
DATED : October 20, 2009
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 442 days.

Signed and Sealed this

Fifth Day of October, 2010

David J. Kappos
*Director of the United States Patent and Trademark Office*